(12) United States Patent
Lortz et al.

(10) Patent No.: US 8,524,284 B2
(45) Date of Patent: Sep. 3, 2013

(54) DISPERSION HAVING AN INSECTICIDAL ACTION

(75) Inventors: Wolfgang Lortz, Wächtersbach (DE); Jochen Scheffler, Alzenau (DE); Gabriele Perlet, Großkrotzenburg (DE)

(73) Assignee: Evonik Degussa GmbH, Essen (DE)

( * ) Notice: Subject to any disclaimer, the term of this patent is extended or adjusted under 35 U.S.C. 154(b) by 1343 days.

(21) Appl. No.: 11/120,627

(22) Filed: May 3, 2005

(65) Prior Publication Data

US 2005/0244513 A1    Nov. 3, 2005

(30) Foreign Application Priority Data

May 3, 2004   (DE) .......................... 10 2004 021 532

(51) Int. Cl.
*A01N 59/00*     (2006.01)
*A01N 25/00*     (2006.01)

(52) U.S. Cl.
USPC .......................................... 424/724; 504/100

(58) Field of Classification Search
None
See application file for complete search history.

(56) References Cited

U.S. PATENT DOCUMENTS

| | | | | |
|---|---|---|---|---|
| 4,443,357 A * | 4/1984 | Maloney et al. | ............. | 516/117 |
| 5,021,083 A | 6/1991 | Schapira et al. | | |
| 5,122,518 A * | 6/1992 | Vrba | .............................. | 514/63 |
| 5,767,107 A * | 6/1998 | Chaundy et al. | ................ | 514/54 |
| 5,830,512 A | 11/1998 | Vrba | | |
| 6,074,987 A * | 6/2000 | Shafer et al. | .................. | 504/132 |
| 6,224,899 B1 | 5/2001 | Misumi et al. | | |
| 6,417,140 B1 | 7/2002 | Patel | | |
| 6,451,731 B1 * | 9/2002 | Agbaje et al. | ................. | 504/118 |
| 2004/0034144 A1 | 2/2004 | Scharfe et al. | | |

FOREIGN PATENT DOCUMENTS

| | | | |
|---|---|---|---|
| DE | 38 35 592 A1 | | 4/1990 |
| DE | EP 0879628 | * | 9/2007 |
| EP | 1 250 048 B1 | | 10/2003 |
| JP | 61-501153 | | 6/1986 |
| JP | 4-208204 | | 7/1992 |
| JP | 7-157401 | | 6/1995 |
| JP | 9-241102 | | 9/1997 |
| JP | 10-258078 | | 9/1998 |
| JP | 2001-122705 | | 5/2001 |
| JP | 2002-306091 | | 10/2002 |
| JP | 2003-238826 | | 8/2003 |
| WO | 85/01949 | | 5/1985 |
| WO | WO 01/35744 A1 | | 5/2001 |
| WO | WO 01/80645 A1 | | 11/2001 |
| WO | WO 2004/089825 A1 | | 10/2004 |

OTHER PUBLICATIONS

English language translation of "Notification of Reasons for Refusal" for JP Pat. Appl. No. 2007-511914 mailed Nov. 5, 2010.

* cited by examiner

*Primary Examiner* — David J Blanchard
*Assistant Examiner* — Tigabu Kassa
(74) *Attorney, Agent, or Firm* — Smith, Gambrell & Russell, LLP

(57) ABSTRACT

Dispersion containing, in addition to water, 0.5 to 20 wt. % of hydrophobic silica, 0.01 to 10 wt. % of a gelling or viscosity-increasing additive, 0.1 to 1 wt. % of a preservative and 0 to 1 wt. % of a surface-active substance. It is prepared by a procedure in which the individual components are dispersed successively or together into the water and in this procedure the individual components are deaerated before and/or during the addition or the dispersion is deaerated during the individual dispersing steps. The dispersion can be employed as an insecticide.

6 Claims, No Drawings

DISPERSION HAVING AN INSECTICIDAL ACTION

INTRODUCTION AND BACKGROUND

The invention relates to a dispersion having an insecticidal action, a process for its preparation and its use.

DE 3835592 discloses the use of hydrophobic $SiO_2$ for combating, for example, sucking insects. Such materials are applied by dusting on.

However, because of the dust nuisance (industrial hygiene) during application of these materials, this procedure is finding ever less acceptance by the user. The aqueous dispersions comprising only a hydrophobic silica and water which are also described in DE 3835592, however, do not show an adequate stability.

U.S. Pat. No. 5,830,512 describes a dispersion in which an adequate stability is achieved by addition of hydrophilic substances, such as, for example, silicas. However, the active hydrophobic component is diluted by a hydrophilic substance as a result of this. Furthermore, only a very low stability of the dispersion of hours to a few days is achieved.

It is known from EP 1 250 048 to stabilize the dispersion of hydrophobic silicon dioxide by gelling additives, such as xanthan gum, sodium alginates or neutralized carboxyvinyl polymers, mixtures of these additives also being possible.

In interplay with the hydrophobic $SiO_2$ particles and incorporated air, these gelling additives moreover have the effect of a significant structural viscosity.

A pronounced structural viscosity offers advantages in application by spraying on: During the spraying process, the viscosity of the dispersion under the shear forces acting on it is relatively low. After the drops of dispersion have impinged on the surface to be covered, the viscosity rises again sharply, so that dripping/running off from perpendicular surfaces in particular is avoided.

The essential feature according to EP 1 250 048 is that in addition to the hydrophobic $SiO_2$ particles to be dispersed, large amounts of air are also incorporated. In conventional dispersing processes, this cannot be avoided without the use of wetting surfactants and defoamers. Thus, a density of only 0.6 g/l is stated in Example 1. Approximately 40% of the volume is therefore air.

To achieve an adequate activity, a minimum mass must be applied to the surfaces to be sprayed. If only approximately 60% of the volume of the spraying equipment can be made use of per spraying operation, this means a significantly reduced efficiency of the staff performing the application.

The transportation and packaging costs and the disposal costs of the packaging required are adversely higher by this proportion.

An approximately 40% larger storage area must also be taken into account during storage.

Furthermore, a homogeneous, bubble-free covering of surfaces to be treated cannot be achieved with a dispersion containing air.

SUMMARY OF THE INVENTION

The present invention provides a dispersion comprising, in addition to water, 0.5 to 20 wt. % of hydrophobic silica, 0.01 to 10 wt. % of a gelling or viscosity-increasing additive, 0.1 to 1 wt. % of a preservative and 0 to 1 wt. % of a surface-active substance.

The water content can be 68 to 99.4 wt. %.

The density of the dispersion can be greater than 0.6 g/ml, preferably 0.7 to 1.02 g/ml.

A pyrogenically prepared, hydrophobized silica can be employed as the hydrophobic silica. It can have a BET surface area of 20 to 600 $m^2/g$.

The gelling or viscosity-increasing additive can be a biopolymer, such as, for example, xanthan gum, sodium alginate, carob bean flour, pectin, agar, carrageens, alginates and/or neutralized carboxyvinyl polymer, or mixtures of these substances.

Preservatives which are approved for foodstuffs can be employed as preservatives. These can be sorbic acid, sodium sorbate, potassium sorbate, calcium sorbate, benzoic acid, sodium benzoate, potassium benzoate, calcium benzoate, PHB ethyl ester, PHB ethyl ester sodium salt, PHB propyl ester, PHB propyl ester sodium salt, PHB methyl ester, PHB methyl ester sodium salt, sulfur dioxide, sodium sulfite, sodium hydrogen sulfite, sodium disulfite, potassium disulfite, calcium disulfite, calcium hydrogen sulfite, biphenyl, orthophenylphenol, sodium orthophenylphenolate, thiabendazole, nisin, natamycin, formic acid, sodium formate, calcium formate, hexamethylenetetramine, dimethyl dicarbonate, propionic acid, sodium propionate, calcium propionate, potassium propionate.

Compounds which are also approved are: nitrates, nitrites, carbon dioxide, chlorine and chlorine dioxide.

Ionic, nonionic and anionic surfactants can be employed as surface-active substances.

The invention also provides a process for the preparation of the dispersion according to the invention, which is characterized in that the individual components are dispersed successively or together into the water and in this procedure the individual components are deaerated before and/or during the addition or the dispersion is deaerated during the individual dispersing steps.

In one embodiment of the invention, the deaeration can be carried out by means of application of a vacuum.

DETAILED DESCRIPTION OF INVENTION

Surprisingly, a stable and active dispersion which does not contain extensive amounts of air can be achieved according to the invention. This deaerated dispersion can be achieved by dispersion of previously deaerated hydrophobic $SiO_2$. A subsequent deaeration of the dispersions is indeed technically possible, but can be achieved only with a high outlay because of the increased viscosity of the homogeneous aqueous phase (gelling agent as an additive). At least the greatest possible portion of the air dispersed in can be removed by deaeration measures before or during the dispersing.

In principle, any dispersing process which either renders possible prior deaeration of the powder to be dispersed and also prevents dispersing in of air during the dispersing is suitable.

One embodiment of the deaeration and dispersing is the utilization of a vacuum dissolver. A procedure is possible here in which water and the gelling additive are predispersed briefly, the entire amount of hydrophobic $SiO_2$ is then added to the surface of the solution, without stirring, the container is evacuated and only then is the dispersing in of the hydrophobic $SiO_2$ started.

A PSI Mix® from NETZSCH can also perform this deaeration of the powder.

In order to remove residual microbubbles, deaeration units, such as the NETZSCH DA-VS vacuum deaerator from NETZSCH, a vacuum thin film rotary process, can be employed.

The dispersion according to the invention can be employed as insecticides, for example, against

| | |
|---|---|
| Housedust mite: | *Dermatophagoides pteronyssinus* |
| Poultry mite: | *Dermanyssus gallinae* |
| Rust-red flour beetle: | *Tribolium castaneum* |
| Grain weevil: | *Sitophilus granarius* |
| Indian meal moth: | *Plodia interpunctella* |
| Wheat aphid: | *Schiazaphis graminum.* |

EXAMPLE 1

477.5 g completely demineralized water are initially introduced into a double-walled dispersing container of the CDS vacuum dispersing system with a DISPERMAT® dissolver from VMA-GETZMANN GMBH, 7.5 g xanthan gum are added, the container is evacuated (water pump) and the components are dispersed/dissolved at 2,000 rpm, toothed disc of 70 mm diameter, for 15 min.

15 g AEROSIL® R 202 are then added, the container is evacuated and the substance is incorporated into the mixture at 800 rpm.

Since air is desorbed by this process and the bubbles formed lead to an increase in volume, the evacuation process must be interrupted several times in order to allow coalescence of the air bubbles and thus an easier deaeration. This operation is repeated until no further increase in volume of the dispersion produced takes place in vacuo. Dispersing is then carried out in vacuo at 3,500 rpm for 15 min.

At a concentration of 3% $SiO_2$ and 1.5% xanthan gum, a density of approximately 0.95 g/ml can be achieved with this method. Theoretically, it should be possible to achieve a density of 1.02 g/ml. This difference can be explained by the formation of some microbubbles.

Such microbubbles result from the release of desorbed air constituents, after competing adsorption has taken place, by a "fine deaeration", for example with the aid of a NETZSCH DA-VS vacuum deaerator the density of approximately 1.02 g/ml can be achieved.

EXAMPLE 2

476.5 g completely demineralized water are initially introduced into a double-walled dispersing container of the CDS vacuum dispersing system with a DISPERMAT® dissolver from VMA-GETZMANN GMBH, 1 g lecithin is added, the container is evacuated briefly (water pump) and the components are dispersed/dissolved at 2,000 rpm, toothed disc of 70 mm diameter, for 1 minute.

7.5 g xanthan gum are then added, the container is evacuated (water pump) and the components are dispersed/dissolved at 2,000 rpm, toothed disc of 70 mm diameter, for 15 min. 15 g AEROSIL® R 202 are then added, the container is evacuated and the substance is incorporated into the mixture at 800 rpm.

Since air is desorbed by this process and the bubbles formed lead to an increase in volume, the evacuation process must be interrupted several times in order to allow coalescence of the air bubbles and thus an easier deaeration. This operation is repeated until no further increase in volume of the dispersion produced takes place in vacuo. Dispersing is then carried out in vacuo at 3,500 rpm for 15 min.

At a concentration of 3% $SiO_2$, 1.5% xanthan gum and 0.2% lecithin, a density of approx. 1.0 g/ml can be achieved with this method.

Due to the presence of a surface-active substance, the wetting of the hydrophobic silica is improved, as a result of which easier deaeration is achieved.

Theoretically, it should be possible to achieve a density of 1.02 g/ml. This difference can be explained by the formation of some microbubbles. Such microbubbles result from the release of desorbed air constituents, after competing adsorption has taken place, by a "fine deaeration", for example with the aid of a NETZSCH DA-VS vacuum deaerator the density of approximately 1.02 g/ml can be achieved.

Conventional additives for preserving, such as sorbic acids/sorbates, benzoic acidibenzoates, propionic acid, parabens (para-hydroxybenzoic acid esters) and/or Acticide® MV (Thor), can be added to the dispersions produced.

EXAMPLE 3

The activity was tested in Petri dishes. In this test, filter papers having a diameter of 8.4 cm were coated on one side, with the aid of a doctor blade, with a layer thickness of 200 μm of the substance to be tested and, after drying, were placed in Petri dishes of plastic having a diameter of 9 cm. The mites (poultry mite, *Dermanyssus gallinae*) were placed in the centre of the treated surface using a fine brush. After application of the mites, the Petri dishes were closed and the lid was additionally secured with Parafilm. The activity tests were evaluated after 24 hours.

All the tests were conducted at a relative atmospheric humidity of 40% and a temperature of 26° C. The activity on the mites was determined by counting under a stereomicroscope. A distinction was made between dead mites, severely damaged mites (severe excitation, mostly lying on the back and unable to run) and living mites in per cent compared with the controls.

The activity was investigated on materials which were produced in accordance with Example 2, dispersions for which other hydrophobic Aerosil types were employed instead of Aerosil® R202 additionally being tested.

0.1% sorbic acid, 0.1% potassium sorbate and 0.2% propionic acid were added as preservatives during the preparation.

A batch without the addition of AEROSIL® was used as a control sample, all the other additives, including the preservatives, being identical.

| AEROSIL ® type | Dead mites | Damaged mites | Living mites | Total mites | Mortality % |
|---|---|---|---|---|---|
| Control sample | 0 | 0 | 103 | 103 | 0 |
| R 805 | 56 | 2 | 52 | 110 | 51 |
| R 974 | 72 | 0 | 42 | 114 | 63 |
| R 202 | 113 | 0 | 0 | 113 | 100 |
| R 812 | 107 | 3 | 9 | 119 | 91 |
| R 812 S | 129 | 0 | 0 | 129 | 100 |
| R 8200 | 121 | 00 | 0 | 121 | 100 |

COMPARISON EXAMPLE 477.5 g completely demineralized water are initially introduced into a double-walled dispersing container of the CDS vacuum dispersing system with a DISPERMAT® dissolver from VMA-GETZMANN GMBH, 7.5 g xanthan gum are added and the components are dispersed/dissolved at 2,000 rpm, toothed disc of 70 mm diameter, for 15 min. Then 15 g AEROSIL® R 202 are added and incorporated into the mixture at 800 rpm. After the incorporation of the AEROSIL® R 202, dispersing is then carried out at 3,500 rpm for 15 min. The dispersion obtained has a density of only 0.6 g/ml.

Further variations and modifications of the foregoing will be apparent to those skilled in the art and are encompassed by the claims appended hereto.

German priority application 10 2004 021 532.4 of May 3, 2004 is relied on and incorporated herein by reference.

We claim:

1. An insecticidal composition which consists of a finely deaerated dispersion of 0.5 to 20 wt. % of hydrophobic silica after-treated with polydimethylsiloxane or hexamethyldisilazane, 0.01 to 10 wt. % of a gelling or viscosity-increasing additive, 0.1 to 1 wt. % of a preservative, and 0 to 1 wt. % of a surfactant in water, wherein desorbed air has been removed by fine deaeration to yield the finely deaerated dispersion having a density of 0.7 to 1.02 g/ml and confer its insecticidal activity.

2. The insecticidal composition according to claim 1, wherein the water content is 68 to 99.4 wt. %.

3. The insecticidal composition according to claim 1, wherein said hydrophobic silica has a BET surface area of 20 to 600 $m^2/g$.

4. The insecticidal composition according to claim 1, wherein the gelling or viscosity-increasing additive is a member selected from the group consisting of xanthan gum, sodium alginate, carob bean flour, pectin, agar, carrageens, alginates, and/or neutralized carboxyvinyl polymer and mixtures thereof.

5. The insecticidal composition according to claim 1, wherein the preservative is a member selected from the group consisting of sorbic acid, sodium sorbate, potassium sorbate, calcium sorbate, benzoic acid, sodium benzoate, potassium benzoate, calcium benzoate, PHB ethyl ester, PHB ethyl ester sodium salt, PHB propyl ester, PHB propyl ester sodium salt, PHB methyl ester, PHB methyl ester sodium salt, sulfur dioxide, sodium sulfite, sodium hydrogen sulfite, sodium disulfite, potassium disulfite, calcium disulfite, calcium hydrogen sulfite, biphenyl, orthoPhenylphenol, sodium orthophenylphenolate, thiabendazole, nisin, natamycin, formic acid, sodium formate, calcium formate, hexamethylenetetramine, dimethyl dicarbonate, propionic acid, sodium propionate, calcium propionate, potassium propionate and mixtures thereof.

6. An insecticidal composition consisting of demineralized water; 3% fumed hydrophobic silica after-treated with polydimethylsiloxane or hexamethyldisilazane; 1.5% xanthan gum; 0.2% lecithin; and a preservative, wherein desorbed air has been removed by fine deaeration to yield a finely deaerated dispersion having a density of approximately 1.0 g/ml, and said finely deaerated dispersion exhibits insecticidal activity.

* * * * *